(12) United States Patent
Boudeville et al.

(10) Patent No.: US 8,268,278 B2
(45) Date of Patent: Sep. 18, 2012

(54) PHOSPHORUS-CALCIUM-STRONTIUM COMPOUND AND USES THEREOF IN ENDODONTIC CEMENTS

(75) Inventors: Philippe Boudeville, Clapiers (FR); Pierre Michailesco, Vendargues (FR); Emmanuel Castany, Villeneuve-les-Maguelone (FR); Michel René Vert, Castelnau-le-Lez (FR)

(73) Assignees: Centre National de la Recherche Scientifique, Paris (FR); Universite de Montpellier I, Montpellier Cedex (FR)

( * ) Notice: Subject to any disclaimer, the term of this patent is extended or adjusted under 35 U.S.C. 154(b) by 673 days.

(21) Appl. No.: 12/373,225

(22) PCT Filed: Jul. 9, 2007

(86) PCT No.: PCT/FR2007/001176
§ 371 (c)(1),
(2), (4) Date: Mar. 20, 2009

(87) PCT Pub. No.: WO2008/006970
PCT Pub. Date: Jan. 17, 2008

(65) Prior Publication Data
US 2010/0068677 A1    Mar. 18, 2010

(30) Foreign Application Priority Data
Jul. 12, 2006   (FR) ..................... 06 06372

(51) Int. Cl.
*C01B 25/32*  (2006.01)
*C01B 25/26*  (2006.01)
(52) U.S. Cl. ........ 423/306; 423/307; 423/305; 423/304; 423/308; 524/436; 524/414; 524/415; 524/416; 524/417

(58) Field of Classification Search .................. 524/436, 524/414, 415, 417; 423/305, 304, 306, 307
See application file for complete search history.

(56) References Cited

U.S. PATENT DOCUMENTS

| 6,593,394 B1 | 7/2003 | Li et al. |
| 7,273,523 B2 * | 9/2007 | Wenz ............................ 106/690 |
| 2008/0027455 A1 * | 1/2008 | Boudeville et al. ............. 606/92 |

FOREIGN PATENT DOCUMENTS

| CN | 1559888 A | * | 1/2005 |
| FR | 2 869 544 A1 | * | 11/2005 |
| GB | 943 678 | * | 12/1963 |
| WO | WO 03/103734 A1 |   | 12/2003 |
| WO | WO 2005/115488 A2 | * | 12/2005 |

OTHER PUBLICATIONS

Kandori et al., Colloids and Surfaces, 1995, 94, 225-230.*
Chabchoub et al., J. Thermal Analysis, 1995, 45, 519-534.*
Kikuchi et al., J. Solid State Chem., 1994, 113, 373-378.*
Database WPI/ Thompson Week 200532, Derwent Publications Ltd., 2005, citing Chinese patent (abstract) 1559888, 2005.
Kandori et al. "Adsorption of protein on non-stoichimetric calcium-strontium hydroxyapatite." Colloids and Surfaces A: Physiochem and Eng. Aspects 94: 225-230, 1995.

* cited by examiner

*Primary Examiner* — Rip A. Lee
(74) *Attorney, Agent, or Firm* — Morgan, Lewis & Bockius LLP (57) ABSTRACT

Phosphorus-calcium-strontium compound of formula (I); method for preparing same; composition for the extemporaneous preparation of a cement comprising a solid phase (SP) and a liquid phase (LP), wherein the solid phase comprises a mixture of inorganic compounds of formula (II); use as an endodontic cement.

39 Claims, 3 Drawing Sheets

PHOSPHORUS-CALCIUM-STRONTIUM COMPOUND AND USES THEREOF IN ENDODONTIC CEMENTS

RELATED APPLICATIONS

The present application is a U.S. National Phase Application of International Application PCT/FR2007/001176, filed Jul. 9, 2007, which claims the benefit of French Application No. 0606372, filed Jul. 12, 2006, all of which are herein incorporated by reference in their entirety.

The present invention relates to a novel phosphorus-calcium-strontium compound, to a method for the preparation thereof and to the use thereof as an endodontic cement.

It also relates to the endodontic cement compositions comprising this novel compound.

Endodontics is a discipline of odontology which concerns the treatment of diseases of the dental pulp (pulpitis, dental abscess, etc).

Pulpitis is the conventional raging toothache: permanent violent pain increased by hot and cold (pulpal hyperemia and inflammation after trauma or caries). Pulpal gangrene occurs when the pulpal inflammation is not treated: bacteria penetrate into the tooth and necrose the pulp. The pain caused (heat, cold, pressure) and the attacks are stronger. When the pulpal necrosis is not treated, the bacteria reach the surrounding alveolar bone and destroy it (periapical lesion), causing a cyst or a granuloma. It is then necessary to depulp the tooth. This lesion generally recovers following disinfection and root filling, in certain cases by endodontic surgery.

Root canal or endodontic treatment is a technique aimed at extirpating the pulp tissue inside the canals or the roots of a tooth, and in shaping, disinfecting and sealing the canal(s) and, in general, the root canal tree, i.e. obtaining a three-dimensional filling.

After exeresis of the pulp, the root canal is mechanically shaped and is chemically disinfected repeated irrigation of the canal with NaClO (at 2.5% active chlorine) and $H_2O_2$ then EDTA (at 5%) in order to remove the maximum amount of pulp debris, of bacteria and of smear layer.

If the pulp is not very inflamed and if the X-ray does not show any trace of a periapical lesion, the mechanical preparation and the chemical disinfection are generally sufficient for good asepsis, and the canal is filled in most commonly by introducing, by means of a lentulo spiral or paste filler (worm screw), a cement based on zinc oxide and on eugenol (ZOE), with optionally a gutta-percha master cone which makes it possible to compact the cement paste before setting in the canal and the adjacent secondary canals, but especially facilitates possible subsequent removal of the filling in the event of a need for retreatment or for putting in a post and core that must support a fixed prosthesis;

more rarely, in order to obtain better sealing of the filling in, the practitioner may have recourse to a compressive technique with gutta-percha (cold lateral, warm vertical or thermomechanical condensation). They are considered to be the reference endodontic techniques and are taught as such in the odontology UFR [training and research units] in France. These techniques have the drawback of being lengthy and of requiring good technical skill by the practitioner.

If there is deep pulp necrosis and/or periapical lesion, after pulp exeresis and preparation, the canal is first treated with calcium hydroxide left in place for a certain amount of time and optionally renewed, before carrying out the filling in as above.

In certain more complex cases, the practitioner may be led to put in, before the filling in, an apical plug or to perform a retrofilling of the apex or else to fill a pathological or accidental perforation of the canal wall. The current material of choice is MTA (Mineral TriOxide Aggregate), a calcium aluminum silicate-based cement.

After the canal has been filled, the coronal part is filled either with a temporary material (Cavit®, etc., IRM®, etc.) if a reintervention is anticipated in the near future, or with a definitive material (amalgam, glass ionomer cement, compomer, composite, etc.), or else by putting in a fixed prosthesis.

The principal materials used in endodontics are calcium hydroxide, zinc oxide-eugenol cements, heavy calcium oxide, MTA and gutta-percha:

calcium hydroxide $Ca(OH)_2$:

The use of calcium hydroxide in endodontics was introduced in 1920 by Hermann (Hermann B W. Calciumhydroxyd als mittle zum behandel und fullen von zahnwurzelkanalen. Wurzburg. *Med Diss* V29, 1920).

Today, calcium hydroxide is more or less unanimously acknowledged to have four qualities (Tronstad L. Endodontie clinique [clinical endodontics]. French translation by Laudenbach P, Medecine-Sciences, Flammarion, Paris 1993, Chap. 5): antimicrobial action, anti-inflammatory action by resolution of exudates which maintain the inflammation, inhibition of dental tissue resorption and induction of hard tissue formation.

Calcium hydroxide also acts as a chemical buffer with respect to the restoration cements, which are generally acidic, and as a thermal buffer with respect to metal restorations. It does not inhibit the polymerization of resins and composites.

However, calcium hydroxide exhibits a certain number of drawbacks:

used alone or as a paste, it does not harden, shrinks on drying and, since it has a nonzero, although low, solubility, it disappears quite rapidly. It does not therefore make it possible to obtain sealed filling in and is used only as a temporary material for disinfecting the canal and treating periapical lesions;

its radiopacity is equal to that of dentine; it is therefore necessary to add to it a contrast product;

when it is used in combination with a resin base for obtaining curing thereof, the latter is in general hydrophobic and limits the diffusion of hydroxyl and calcium ions, hence a virtually negligible antimicrobial effect.

Zinc oxide-eugenol (ZOE) cements:

Eugenol or 4-allyl-2-methoxyphenol constitutes 96% by weight of clove essence. It reacts, via its phenol function, with zinc oxide ZnO to give a zinc eugenolate.

The biological properties of ZOE cements are essentially due to the presence of eugenol. It has a sedative effect on pain during pulpitis. It exhibits an average antimicrobial activity. Finally, it can be easily introduced into the root canals using a lentulo spiral.

ZOE cements are mainly used at the bottom of a cavity, for pulp capping and root canal filling.

ZOE cements also have a certain number of drawbacks: a characteristic smell of clove, slight shrinking on setting, hence the need for recourse to gutta-percha cones in order to improve the sealing, a nonzero solubility and a fleeting antimicrobial effect. ZOE cements do not offer any protection over the long term.

"Heavy" calcium oxide, known under the trademark Biocalex®, is a product based on "heavy" calcium oxide CaO, a precursor for calcium hydroxide by hydration with a high expansion coefficient, which confers on it an antimicrobial effect and provides good sealing of the fillings. However, its use is not without drawbacks: considerable risk of the tooth breaking up, weak mechanical characteristics.

MTA (Mineral Trioxide Aggregate):

MTA is a portland-type cement based on calcium aluminum silicate. The presence of calcium oxide is reflected by a certain alkalinity when setting occurs, which is favorable to an antimicrobial activity and to the induction of the dentinogenesis process. It provides good sealing. Its indications are: pulp capping, apexification, the creation of an apical plug, the repair of perforations and retrofilling. It is not, however, used for the complete filling in of a canal due to its lack of fluidity and to the fact that, once set, its strength is too great to allow removal of the filling.

Gutta-percha:

Gutta-percha, or trans-1,4-polyisoprene, is a natural polymer extracted from a tree, Palaquium gutta-bail. It is incompressible but thermoplastic above 60° C., which allows it to take the shape of the endodontium. It becomes rigid on cooling.

It is always used in combination with a thin coat of cement (generally a slow-setting ZOE cement). Although compressive techniques are considered to be the reference techniques, they are rarely carried out routinely because they require much too long a procedure time which is incompatible with the current repertoire of professional actions. Furthermore, they require the practitioner to have good technical skills necessitating a specific training.

Calcium phosphate cements have been cited several times in the literature, with the possibility of use in endodontics being mentioned (U.S. Pat. No. 4,518,430 and U.S. Pat. No. 5,997,624). However, most of the publications and applications relating to this biomaterial concern orthopedics.

The formula of the first calcium phosphate cement for dental use, based on calcium oxide and orthophosphoric acid, was published in 1832. However, this product was very quickly replaced by zinc phosphate cements, which have a much greater mechanical strength and are much more resistant to chemical erosion.

The calcium phosphate hydraulic cements for orthopedic use are obtained by mixing a powder containing a calcium phosphate which is acidic in nature and a calcium phosphate which is basic in nature with water or a buffered aqueous solution. The solid compounds dissolve in the aqueous phase and the calcium and phosphate ions thus released will reprecipitate in a the form o a calcium phosphate with an intermediate basicity less soluble than the starting products calcium hydrogen phosphate dihydrate (brushite or DCPD) or stoichiometric hydroxyapatite (HA) or calcium-deficient hydroxyapatite (CDHA). It is the entanglement of the precipitated crystals that will ensure the mechanical characteristics of the cement. For example:

When the cements based on calcium oxide and on calcium hydrogen phosphate or on calcium dihydrogen phosphate are mixed with water for the purpose of their use, they give hydroxyapatite and possibly calcium hydroxide (depending on the amount of CaO used).

With an excess of calcium oxide, these cements are too basic for use in orthopedics as a bone replacement material, but they are perfectly suitable for filling treatments in endodontics.

This type of cement has a satisfactory antimicrobial activity as long as a Ca/P=2 ratio is achieved, and an antimicrobial activity comparable to that of pure calcium hydroxide as long as a Ca/P=2.5 ratio is achieved. However, these cements have several deficiencies which make their use in treatment difficult to envision: they are difficult to handle compared with ZOE cements, and they are not radiopaque.

It is necessary for a root canal filling cement to be radiopaque for two reasons. The radiopacity makes it possible to verify that the canal is correctly filled and to rapidly determine whether or not a tooth has already been treated in the case where the patient is not a regular patient. The radiopacity of a root canal filling cement is, moreover, obligatory in order for the treatment to be paid for by health insurance Now, this type of cement, which has a composition identical to that of dentine and enamel, has a radiopacity which is equivalent and not greater.

The addition, to the formula of the cement, of a radiopaque compound such as a barium salt can be envisioned, but it would result in a deterioration of the mechanical and antimicrobial properties of the cement.

The cement must be easy for the practitioner to handle so as not to discourage the latter despite the qualities of the product. The preparation of cements based on calcium oxide and on calcium hydrogen phosphate (mixing of the powder with the liquid) is simple and identical to that of zinc phosphate and ZOE cements. On the other hand, they do not hold perfectly on the lentulo spiral and, while it is possible to introduce the cement into extracted teeth (ex vivo laboratory test), this will be much more difficult on a patient in surgery.

The basis of the invention is therefore the development of a cement for endodontic use, in particular for filling root canals of depulped teeth, this cement having good mechanical properties, long-lasting antimicrobial properties, and a rheology which enables it to be implanted under go conditions, in addition, a cement which is radiopaque and expansive when it sets and which thus takes on the role of a leak tight filling of the canal to be filled, completing the panel of the positive properties of the cement, has been developed.

The development of this cement was based on method for producing of a novel phosphorus-calcium-strontium compound which corresponds to formula (I) below:

$$Ca_{(1-x)}Sr_{(x)}HPO_4 \qquad (I)$$

in which x represents a number between 0.2 and 0.8, preferably between 0 3 and 0.7, even more preferably between 0.4 and 0.6, and advantageously between 0.45 and 0.35.

The document Chabchoub S. et al., Journal of Thermal Analysis, 1995, 45(3), 519-534, studies the possibility of forming solid $Ca_{(1-x)}Sr_xHPO_4$ solutions by substitution of the calcium with strontium in calcium hydrogen phosphate and, conversely in the $CaHPO_4$—$SrHPO_4$—$H_2O$ system, by establishment of the water-solubility diagram of the ternary mixture (1-x) $CaCo_3 \times SrCo_3 + H_3PO_4$. They note that Ca replaces Sr to give a solid solution which keeps the structure of $\alpha$-$SrHPO_4$ with a decrease in the lattice parameters for 0.6<x<1, and that Sr replaces Ca to give a solid solution which keeps the structure of $CaHPO_4$ with an increase in the lattice parameters for 0.05<x<0.25. Finally, for 0.25<x<0.6, the mixture is a two-phase mixture and contains variable proportions of $Ca_{0.75}Sr_{0.25}HPO_4$ and of $Ca_{0.4}Sr_{0.6}HPO_4$. However, they are prepared by methods of precipitation in solution with an equilibrium being reached, in which the position of said equilibrium depends on various experimental parameters, and which, consequently, cannot be used on an industrial scale or quite simply to reproducibly obtain a chosen compound. Nowhere does this document mention the use of such a compound for preparing a dental cement.

The document Kikuchi M. et al., Journal of Solid State Chemistry, 1994, 113(2), 373-378, also relates to the analysis of strontium-substituted hydroxyapatite crystals, without a method for the reproducible or able production being described therein for chosen compound. This compound is characterized by a (Ca+Sr)/P ratio=1.67, which is different than that of the invention (Ca+Sr)/P=1.0 and could not in any w substitute therefor.

The compound of formula (I) with x between 0.45 and 0.55 is novel and constitutes a first subject matter of the invention. This compound, which keeps the structure of $CaHPO_4$, lies within a range where, according to Chabchoub S. et al., a two-phase mixture is obtained (see above). It can be obtained by virtue of the particular method for the synthesis thereof, which makes it possible to work outside the kinetic and conventional thermodynamic equilibria of dissolution-precipitation in aqueous solution.

The compound of formula (1) is a mixed anhydrous strontium and calcium hydrogen phosphate. According to the invention, this compound is prepared by mechanosynthesis from calcium his (dihydrogen phosphate) monohydrate (or MCPM, mcnocalcium phosphate monohydrate; and from strontium hydroxide octahydrate, and optionally from orthophosphoric acid, or from calcium hydroxide, i.e. it comprises a step of mixing the starting products in solid form, according to the reaction:

For $0.5 \leq x \leq 0.8$ $(1-x)Ca(H_2PO_4)_2.H_2O+(2x-1)H_3PO_4+x\ Sr(OH)_2.8H_2O \rightarrow Ca_{(1-x)}Sr_xHPO_4+(9x+1)H_2O$ For $0.2 \leq x \leq 0.5$ $Ca(H_2PO_4)_2.H_2O+2x\ Sr(OH)_2.8H_2O+(1-2x)Ca(OH)_2 \rightarrow 2Ca_{(1-x)}Sr_xHPO_4-(16x+3)H_2O$ In particular in the case where x=0.5:

$Ca(H_2PO_4)_2.H_2O+Sr(OH)_2.8H_2O \rightarrow 2Ca_{0.5}Sr_{0.5}HPO_4+11H_2O$

The mixing of the starting products of the reaction may be carried out in a ball mill or by simple mixing in a mortar. In practice, any means of mechanical stirring of the powders is suitable for the preparation of the compound of formula (I). A small amount of water (optionally containing orthophosphoric acid $H_3PO_4$ or calcium hydroxide) may be introduced into in the mixer in order to facilitate the mixing of the powders.

The reaction is carried out at ambient temperature; it may require a mixing time ranging from a few minutes to one hour. The product is subsequently dried by any means known to those skilled in the art, for instance by passing it through an oven or an incubator or by atomization. The heating of the product of the invention may also be carried out under reduced pressure so as to facilitate evaporation of the water.

The document Yokogawa Y. et al., Chemistry Letters, 1996, 45(4), 161-166, describes a wet mechanochemical method for preparing a calcium- and strontium-deficient apatite starting from $CaHPO_4.2H_2O$, $CaCO_3$, $SrHPO_4$ and $Sr(OH)_2.8H_2O$. However, the conditions of this method are not the most favorable, as shown by the inventors (Boudeville et al., Key Engineering. Materials 2004; 254-256: 103-106), and cannot produce the compound of formula (I).

The compound of formula (I) comprises strontium. The latter plays an important role in the bone mineralization process: it is naturally present in the mineral phase of bones, it readily replaces calcium in bone, it stimulates the activity of osteoblasts while at the same time partially inhibiting that of osteoclasts, and it reinforces bone solidity. For these reasons, it is used in the treatment per os of post-menopausal osteoporosis. Furthermore, it is more radiopaque than calcium.

In the case of the treatment of a tooth by filling of the pulp canal, strontium may be expected to have a stimulating activity on the activity of odontoblasts (pulp cells) and on cementoblasts (cement which surround and protect the dentine).

The introduction of strontium into the compound of formula (I), in the perspective of use for the preparation of an endodontic cement, brings three things:

(i) it has a higher atomic mass than calcium and makes the cement more radiopaque;

(ii) in the form used, it contributes to the setting reaction, the calcium and strontium apatites forming a continuous solid solution, unlike the barium salts conventionally used for increasing the radiopacity;

(iii) since it stimulates the activity osteoblasts, it may be expected to also stimulate the activity of cementoblasts for the formation of the apical plug (or barrier), the best guarantee for preventing the development or the return of a periapical lesion.

Cements used as bone substitutes, based on calcium hydrogen phosphate dihydrate ($CaHPO_4.2H_2O$), on calcium oxide (CaO) and on strontium carbonate, are known in the prior art, in particular through WO 2005/115488. However, in such a cement composition, the strontium contributes only partly to the setting reaction, the strontium salt is dispersed in the calcium hydroxyapatite phase and it increases the mechanical properties thereof.

The cements described in this document are intended for orthopedic use: injectable or composite bone substitute containing microspheres of a polymer which is rapidly biodegradable, in order to create potential macroporosities therein, while the cement of the invention is for endodontic use for the treatment and filling of root canals, with introduction using a lentulo spiral, and should be microporous.

Their compositions are different:

Orthopedic Cement:

solid phase: $6CaHPO_4.2H_2O+2.5\ CaO+1.5\ SrCO_3$ (60% m/m)+PLAGA (40% m/m) (PLAGA=microspheres of poly (DL-lactic acid-co-glycolic acid));

liquid phase 0.75 M ammonium phosphate buffer, pH 7, and liquid/powder ratio=0.5 ml $g^{-1}$.

In the prior art cement, Cao is deficient so as to obtain a neutral cement; in that of the invention, there is a large excess of CaO so as to obtain, by virtue of the hydration thereof, the expansion necessary for the sealing of the filling and a rapid and long-term antimicrobial activity; the strontium therein is also in greater amount so as to have sufficient radiopacity.

A mixed anhydrous calcium and strontium hydrogen phosphate is mentioned in WO 2005/115486, without an industrial method for preparing such a compound being described. The use of such a compound in a bone cement is also not described.

Document CN-1559888 describes a bone cement based on calcium hydrogen phosphate, strontium hydrogen phosphate and tetracalcium oxodiphosphate (or tetracalcium phosphate, TTCP). The compound of formula (I) is not used in this cement which results from the mixture:

solid phase: $Ca_4(PO_4)_2O+CaHPO_4+SrHPO_4$ liquid phase: aqueous solution of $H_3PO_4$ at 0.5-1 mol/l.

This cement has very good mechanical properties, essentially due to the TTCP, which are suitable for use in bone, but which would not enable a reintervention if the cement was applied to a tooth. Its rheology is not suitable for root canal filling.

This cement does not release hydroxyl ions, it is therefore devoid of any antimicrobial effect. It does not produce any expansion during its setting reaction and does not therefore have the hermeticity properties desired in endodontic use.

In addition, the starting product, $Ca_4(PO_4)_2O$, is not commercially available and is difficult to prepare.

Another subject of the invention is composition for the extemporaneous preparation of a cement, comprising a solid phase (SP) and a liquid phase (LP) which are separate. The solid phase comprises a mineral mixture of formula (II):

$$6Ca_{(1-x)}Sr_{(x)}HPO_4 + y\, CaO + z\, A \qquad (II)$$

in which:

x represents a number between 0.2 and 0.8, as in formula (I) above and with the same preferred variants;

v represents a number between 5 and 12;

A represents a radiopacifying compound;

z represents a number between 1 and 3.

A may be a bismuth salt, barium salt or strontium salt in carbonate, sulfate, fluoride or phosphate form.

When the intended use is the filling of the endodontic canal, y is preferably chosen between 7 and 12, preferably between 8 and 10, for the cement of formula (II).

When the intended use is pulp capping, cement compositions in which y is between 5 and 7 are preferred. Preferably, z is between 1.5 and 2.5.

The cement of the invention is biocompatible and injectable. It is potentially biodegradable.

The mixture of formula (II) is prepared by mixing, in the form of powders, the mixed calcium and strontium hydrogen phosphate of formula (I), the calcium oxide (CaO) and the radiopaque compound (A) in the proportions of formula (II).

The liquid phase of the cement composition is constituted of water or of an aqueous saline solution of pH between 5 and 9. Preferably, an aqueous saline elution of pH between 6 and 8, preferably between 6.5 and 7 is used. Advantageously, an aqueous solution comprising from 0.2 to 1.5 mol/l of a mixture of $NaH_2PO_4$ and of $Na_2HPO_4$ buffer an aqueous solution comprising from 0.2 to 1.5 mol/l of a mixture of $NaH_2PO_4$ and of sodium glycerophosphate hexahydrate (NaGP buffer), or an solution comprising 0.2 to 1.5 mol/l of a mixture $NH_4H_2PO_4$ and of $(NH_4))_2HPO_4$ (NH4P buffer) or else an aqueous solution comprising from 0.2 to 1.5 mol/l or trisodium citrate (Cit buffer), is used.

Advantageously, the cement composition of the invention also comprises at least one polymer. One or other of the solid phase (SP) or the liquid phase (LP) of the cement composition of the invention may comprise this or these polymer(s).

The polymer may be an alginate, chitosan, dextran, dextran sulfate or a polyacrylate.

Advantageously, the polymer is chosen from polyacrylates, such as sodium polyacrylate, and alginates, such as sodium alginate. Preferably, a polyacrylate having a molecular weight of between 2000 and 50 000, advantageously between 3000 and 30 000, even more advantageously between 5000 and 20 000, is chosen. Such polymers are commercially available.

According to the invention, when the polymer is added to the solid phase, it represents from 1% to 5% by weight relative to the total weight of the solid phase of the cement composition, advantageously from 2% to 4%. If the polymer is added to the liquid phase, it represents from 0.2% to 10% by weight relative to the total volume of the liquid phase. The amount of polymer to be used in the composition varies within these ranges according to the nature of the polymer.

Preferably, the liquid phase also comprises a small amount of a conventional antimicrobial such as NaClO.

The ratio between the volume of the liquid phase (L) and the weight of the solid phase (P) when the cement composition is prepared is 0.2<L/P<0.7 ml/g, advantageously between 0.3<L/P<0.6 ml/g. When the intended use is root canal filling, 0.4<L/P<0.5 ml/g is preferred; when the use is pulp capping, 0.35<L/P<0.4 ml/g is preferred.

When the solid phase is mixed with the liquid phase, the mixed calcium and strontium hydrogen phosphate reacts with the calcium oxide according to the scheme below:

$$6Ca_{(1-x)}Sr_xHPO_4 + y\, CaO \rightarrow Ca_{(10-6x)}Sr_{6x}(PO_4)_6(OH)_2 + (y-4)Ca(OH)_2$$

and the hydroxyapatite precipitates a brief period of time (a few minutes) after it has been brought into contact with the liquid phase.

According to one variant of the invention, the compound $6Ca_{(1-x)}Sr_xHPO_4$ can be replaced, in this step, with its precursor, which is a mixture of $CaHPO_4.2H_2O$, or of $CaHPO_4$, and of $SrHPO_4$.

Indeed, $6Ca_{(1-x)}Sr_xHPO_4 = 6(1-x)CaHPO_4(2H_2O) + 6xSrHPO_4$

By replacing, in the formulation of the cement (II), the compound (I) with a mixture of $CaHPO_4.2H_2O$, or $CaHPO_4$, and of $SrHPO_4$, according to the equation above, cements that can be used in endodontics are also obtained. When this mixture is used as a replacement for the compound (I) in the formulation (II), the same final product is obtained after mixing with the liquid phase and setting reaction.

Another subject of the invention is therefore a composition for the extemporaneous preparation of a cement, comprising a solid phase (SP) and a liquid phase (LP) which are separate, the solid phase comprising a mineral mixture of formula (IIa):

$$6(1-x)CaHPO_4(2H_2O) + 6xSrHPO_4 + y\, CaO + z\, A \qquad (IIa)$$

in which x, y, z and A have the same meaning as above in formula (II), the other constituents, liquid phase and polymer, being identical to those described above.

Another subject of the invention is a method for preparing a cement, starting from a composition comprising a solid phase and a liquid phase described above, and comprising least one step in which the solid phase is mixed with the liquid phase, in which step the reaction for formation of a mixed calcium and strontium hydroxyapatite takes place according to the scheme above.

Throughout the duration of the storage, the cement is stored in the form of two phases, one solid, the other liquid, separately. The cement compositions of the invention have good storage properties as long as the solid phase is kept in an air-tight and moisture-tight packaging.

Another subject of the invention is a dental kit comprising a composition for the extemporaneous preparation of a cement, as described above, in the form of a liquid phase and a solid phase that are stored in separate compartments.

Such a kit intended for dental root canal filling or for another dental use may be constituted of two distinct bottles, of volumes suitable for consumption by dental surgeries.

Kits in the form of bottles each comprising the amount of solid phase and of liquid phase suitable for filling a single tooth may also be envisioned. Such packaging has the advantage of preventing dosage errors at the time the cement is prepared and a possible deterioration of the qualities of the cement due to the repeated opening of the bottles.

It is also possible to envision packaging the cement composition of the invention in a container for direct extemporaneous mixing such as a cartridge. Mention may, for example, be made of the mixing device described in U.S. Pat. No. 5,549,380 which makes it possible to introduce the liquid phase into the solid phase by suction at the time when the mixing should be carried out. A soft pouch with two compartments, each containing one of the phases of the composition, the compartments being separated by a seal which is broken at the time when the mixing should be carried out, allowing the liquid phase to pass into the compartment containing the solid phase, may also be used.

The presence of strontium in the hydroxyapatite makes it possible have a radiopaque cement without deterioration of the mechanical and theological properties of the cement: setting time, compressive strength and injectability.

A regular release of $Sr^{2+}$ ions from the set cement is also observed, the $Sr^{2+}$ ions being capable of activating dentine reconstruction by activation of the odontoblasts.

During the setting reaction, the cement of the invention produces a slight expansion, sufficient to ensure that the filling is sealed and insufficient to cause pain or weaken the tooth.

The cement compositions of the invention also have the property of releasing $OH^-$ ions in a regular and sustained manner, thereby explaining their antibacterial activity. These compositions have a hardness that is sufficient for them to be used in the filling of a root canal. However, they have a hardness that is slightly less than that of dentine, thereby making it possible to envision removing them in the event of the formation of a new periapical lesion.

The preferred uses of this cement composition are the following:

Filling of dental root canals subsequent to pulpectomy. This filling is advantageously performed after having repeatedly applied calcium dihydroxide $Ca(OH)_2$ in order to bring about resorption the periapical lesion.

Pulp capping (direct and indirect): an adaptation of the composition and of the liquid phase/solid chase ratio makes it possible to adapt the formulation for this use in such a way as to have a shorter setting time and a lesser alkalinity. In this use, the composition of the invention should promote the formation of a cicatricial dental bridge.

Repair of a perforation.

Formation of an apical plug.

The cement compositions of the invention also have the advantage of being compatible with the presence if residues in bleach in the dental canal. In fact, after pulpectomy, the dentist cleans the dental canal with a solution of sodium hypochlorite, and then optionally of EDTA or of $H_2O_2$. Perfect drying of the root walls is required before putting in conventional cements which are often immiscible with an aqueous phase, with the risk of formation of a hiatus. This is not the case of the cement of the invention. Insufficient rinsing of the dental canal will not impair the setting of this cement.

FIGURES

RIZ: relative inhibition zone, i.e. compared with the inhibition by the freshly prepared samples of pure calcium hydroxide (ZIR=1 for $Ca(OH)_2$).

EXAMPLES

Example 1

Preparation of the Mixed Calcium-Strontium Hydrogen Phosphate $Ca_{0.5}Sr_{0.5}HPO_4$ This compound was prepared by mechanosynthesis from MCPM and strontium hydroxide octahydrate under the following conditions:

Milling for 20 min, Fritsch Pulverisette 6 planetary mill, eccentricity 6 cm, 500 ml porcelain bowl, 4 porcelain balls 30 mm in diameter, total mass 248 g, total surface area 113 cm², rotational speed 200 rpm.

After milling 20 min, a pasty mass is obtained due to the presence of water resulting from the reaction (38.3%). The paste is then dried for 3 h at 120° C. The cake is manually crushed and the powder is screened (100 μm screen). Approximately 150-160 g of screened powder are thus obtained, i.e. a yield of 80-83%.

Example 2

Spray Drying of the Mixed Calcium-Strontium Hydrogen Phosphate $Ca_{0.5}Sr_{0.5}HPO_4$ 1300 ml of distilled water are added to 1200 g of paste prepared in four steps as in example 1 and containing 740 g of $Ca_{0.5}Sr_{0.5}HPO_4$ and 460 g of water (ratio of mass of powder to mass of suspension of 30%). The suspension was spray dried (Niro Atomizer Minor, oven temperature 105° C., air pressure 7 bar). 630 g of dry powder are recovered (yield 85%), 80% of the mass of which has a particle size of less than 50 μm.

Example 3

Preparation of a Composition of Endodontic Cement with Strontium Fluoride as Radiopacifier (Referred to as OP3F)

*Solid Phase
Mixture $6Ca_{0.5}Sr_{0.5}HPO_4+9CaO+2SrF_2$
*Liquid Phase
Buffer solution of $NaH_2PO_4+Na_2HPO_4$ at 0.25 mol per liter with respect to phosphate, +sodium citrate at 0.25 mol per liter with respect to citrate+sodium polyacrylate (M=5100) to give 5% by mass/volume
*Liquid to Powder (L/P) Ratio
The powder is mixed with the liquid phase in a ratio of 0.5 ml of liquid per gram of powder, i.e. L/P=0.5 ml g$^{-1}$. During the various tests, the two components were mixed on a glass plate at ambient temperature of 27° C. using a spatula. The axial compressive strength is 4 MPa, the setting time is 16 min and the correct hold time on the paste filler (lentulo spiral) is 10 min.

Example 4

Preparation of a Composition of Endodontic Cement with Strontium Carbonate as Radio-Pacifier (referred to as OP3)

*Solid Phase

Mixture $6Ca_{0.5}Sr_{0.5}HPO_4 + 9CaO + 2SrCO_3$ to give 97% by mass+sodium polyacrylate (M=20 000) to give 3% by mass

*Liquid Phase

Buffer solution of $NaH_2PO_4 + Na_2HPO_4$, pH=7, 0.5 mol per liter with respect to phosphate, +NaClO containing 0.02% of active Cl (the sodium hypochlorite is there only as an antimicrobial and antifungal agent for preventing the development of a microbial or fungal flora in the buffer over time after the latter has been opened).

*Liquid to Powder (L/P) Ratio

The powder is mixed with the liquid phase in a ratio of 0.4 ml of liquid per gram of powder, i.e. L/P=0.4 ml g$^{-1}$. During the various tests, the two components were mixed on a glass plate at 20° C.±2° C. using a spatula. The mixture may also be prepared by milling with a pestle in a mortar or by mechanical stirring of a capsule containing the desired amount of the two phases (as for amalgams or zinc phosphate cements); technique tested using an HSM 1 capsule mixer for 15 s.

Figure 1:
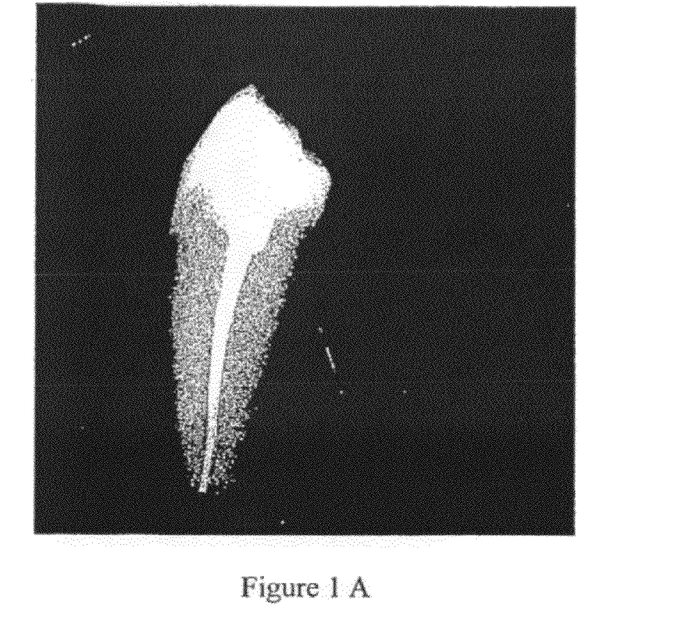
FIG. 1A: Radiology of a tooth filled with a ZOE cement.
FIG. 1B: X-ray photograph of a tooth filled with the cement of example 4 (OP3).

Radiographic Characteristics:

As can be noted on FIGS. 1A and 1B, the cement of the invention has a radiopacity equivalent to that of 3.2 mm of aluminum, comparable to that of a commonly used ZOE cement.

Mechanical Properties:

Various cement compositions were tested for their mechanical properties, on the basis of the composition of example 4, by varying the P/L ratio. The results are shown in Table 1 below:

Microbiological Properties:

The antimicrobial activity of the OP3 cement was compared with that of a conventional ZOE cement and with that of a pure calcium hydroxide paste; test for inhibition of growth of a polymicrobial inoculum taken from dental plaque, by diffusion in a solid agar medium. The activity of these two cements was verified on freshly prepared samples of cement and samples prepared 13 days previously. The fresh OP3 (RIZ=1.26) and the fresh ZOE (RIZ=1.23) exhibited a greater antimicrobial activity than that of the calcium hydroxide (RIZ=1 for $Ca(OH)_2$); p≈10$^{-5}$, 1-factor ANOVA test. On the other hand, when prepared 13 days previously, the activity of the OP3 remains equivalent to that of the fresh calcium hydroxide (P=0.07), whereas that of the ZOE cement is virtually zero (7 of the 8 samples did not show any inhibition), as could be expected according to the literature.

Figure 2:
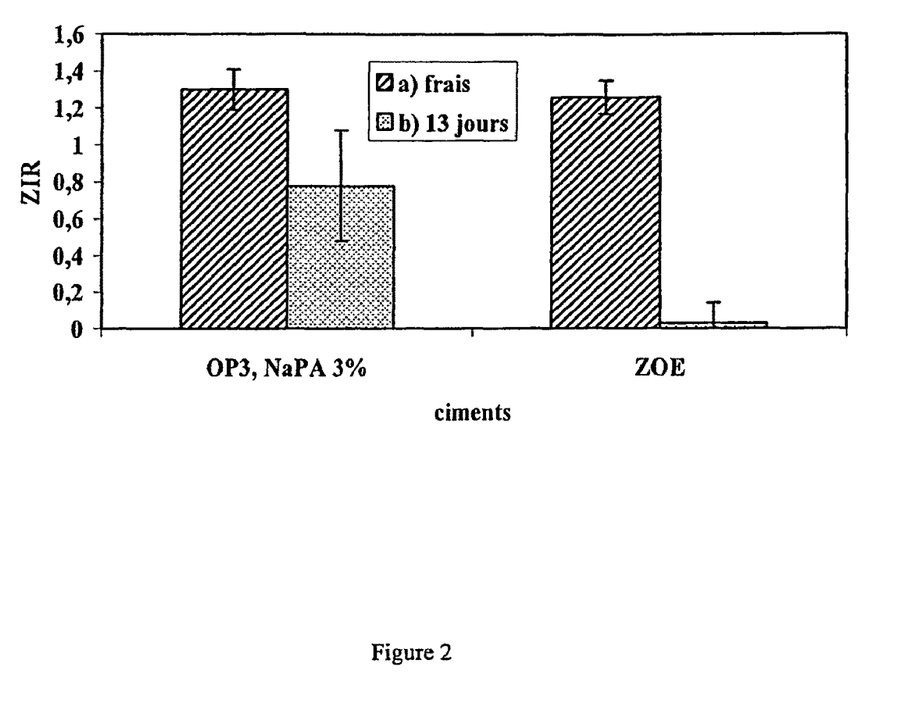
FIG. 2: Inhibition of growth of a polymicrobial inoculum (test by diffusion in solid agar medium) by the OP3 cement and a conventional ZOE cement (a) freshly prepared and (b) prepared 13 days previously.

These results are shown in FIG. 2.

Figure 3:
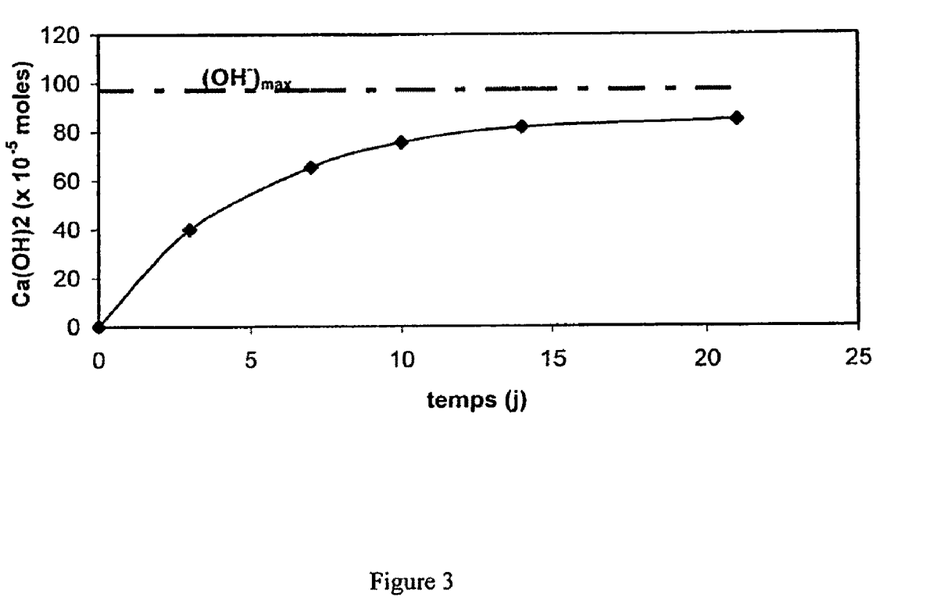
FIG. 3: Cumulative amount of hydroxyl ions released over time from the OP3 cement; the horizontal straight line represents the maximum releasable amount.

Release of Hydroxyl Ions:

Cylindrical samples of 0.5 g were immersed in 10 ml of distilled water. The latter was renewed periodically and the hydroxyl ions released were assayed by pH-metry (FIG. 3).

The sustained release of hydroxyl ions explains the antimicrobial activity of this cement and the diffusion of said ions in dentine tubules enables the latter to be disinfected. Said ions are released only on contact with an aqueous phase which, once the cement has been introduced into the root canal, is much smaller relative to the mass of the cement than in the in vitro test. The antimicrobial protective effect of this cement in vivo should therefore be much longer lasting than in this 3 week in vitro test.

Handleability:

During the preparation of the OP3 cement, it is noted that an excellent consistency, good hold on the lentulo spiral, and a viscosity suitable for clinical use are obtained.

The invention claimed is:

1. A compound corresponding to formula (I) below:

$$Ca_{(1-x)}Sr_{(x)}HPO_4 \quad (I)$$

in which x represents a number between 0.45 and 0.55.

2. A method for producing a compound of formula (I):

$$Ca_{(1-x)}Sr_{(x)}HPO_4 \quad (I)$$

in which x represents a number between 0.2 and 0.8, comprising a step of mixing calcium bis(dihydrogen phosphate) monohydrate and strontium hydroxide octahydrate in powder form: according to one of the reactions:

For 0.5<x<0.8

$$(1-x)Ca(H_2PO_4)_2 \cdot H_2O + (2x-1)H_3PO_4 + x\,Sr(OH)_2 \cdot 8H_2O \rightarrow Ca_{(1-x)}Sr_{(x)}HPO_4 + (9x+1)H_2O$$

For 0.2<x<0.5

$$Ca(H_2PO_4)_2 \cdot H_2O + 2x\,Sr(OH)_2 \cdot 8H_2O + (1-2x)Ca(OH)_2 \rightarrow Ca_{(1-x)}Sr_{(x)}HPO_4 + (16x+3)H_2O.$$

| Cements | L/P ratio (ml · g$^{-1}$) | Axial compressive strength (MPa) | Consistency and handling (score: 0 to 5) | Initial setting time at 37° C. (min) | Final setting time at 37° C. (min) | Expansion (as %) |
|---|---|---|---|---|---|---|
| OP3, NaPA 3% | 0.35 | 13 | 1 | 9 | 12 | 3.3 |
| OP3, NaPA 3% | 0.38 | 9.9 | 5 | 11 | 14 | 3.4 |
| OP3, NaPA 3% | 0.4 | 8.9 | 5 | 13 | 16 | 3.1 |
| OP3, NaPA 3% | 0.45 | 7.5 | 1 | 17 | 21 | 2.9 |

3. The method as claimed in claim 2, wherein the mixing of the mixture is carried out in the presence of orthophosphoric acid or of calcium hydroxide.

4. A composition for the extemporaneous preparation of a cement, comprising a solid phase (SP) and a liquid phase (LP), wherein the solid phase comprises a mixture of mineral compounds of formula (IIa):

$$6(1-x)CaHPO_4(2H_2O) + 6xSrHPO_4 + y\,CaO + z\,A \quad (IIa)$$

in which:
x represents a number between 0.2 and 0.8;
y represents a number between 5 and 12;
A represents a radiopaque compound;
z represents a number between 1 and 3.

5. A composition for the extemporaneous preparation of a cement, comprising a solid phase (SP) and a liquid phase (LP), wherein the solid phase comprises a mixture of mineral compounds of formula (II):

$$6Ca_{(1-x)}Sr_{(x)}HPO_4 + y\, CaO + z\, A \quad (II)$$

in which:
x represents a number between 0.2 and 0.8;
y represents a number between 5 and 12;
A represents a radiopaque compound;
z represents a number between 1 and 3.

6. The composition as claimed in claim 5, in which x represents a number between 0.3 and 0.7.

7. The composition as claimed in claim 5, wherein x represents a number between 0.4 and 0.6.

8. The composition as claimed in claim 5, wherein x represents a number between 0.45 and 0.55.

9. The composition as claimed in claim 5, in which A is bismuth salt, a barium salt or a strontium salt.

10. The composition as claimed in claim 5, wherein A is a carbonate, a sulfate, a fluoride or a phosphate.

11. The composition as claimed in claim 5, wherein y is chosen between 7 and 12.

12. The composition as claimed in claim 5, wherein y is chosen between 5 and 7.

13. The composition as claimed in claim 5, wherein y is chosen between 8 and 10.

14. The composition as claimed in claim 5, wherein z is between 1.5 and 2.5.

15. The composition as claimed in claim 5, wherein the liquid phase is constituted of water or of an aqueous saline solution of pH between 5 and 9.

16. The composition as claimed in claim 15, wherein the liquid phase is an aqueous saline solution of pH between 6 and 8.

17. The composition as claimed in claim 15, wherein the liquid phase is an aqueous saline solution of pH between 6.5 and 7.5.

18. The composition as claimed in claim 15, wherein the liquid phase is:
an aqueous solution comprising from 0.2 to 1.5 mol/l of a mixture of $NaH_2PO_4$ and of $Na_2HPO_4$,
an aqueous solution comprising from 0.2 to 1.5 mol/l of a mixture of $NaH_2PO_4$ and of sodium glycerophosphate hexahydrate,
an aqueous solution comprising 0.2 to 1.5 mol/l of a mixture of $NH_4H_2PO_4$ and of $(NH_4)_2HPO_4$, or
an aqueous solution comprising 0.2 to 1.5 mol/l of trisodium citrate.

19. The composition as claimed in claim 5, wherein the ratio between the volume of the liquid phase (L) and the weight of the solid phase (P) is 0.3<L/P<0.6 ml/g.

20. The composition as claimed in claim 5, wherein the ratio between the volume of the liquid phase (L) and the weight of the solid phase (P) is 0.2<L/P<0.7 ml/g.

21. The composition as claimed in claim 20, wherein 0.4<L/P<0.5 ml/g.

22. The composition as claimed in claim 20, wherein 0.35<L/P<0.4 ml/g.

23. The composition as claimed in claim 5, further comprising at least one polymer.

24. The composition as claimed in claim 23, wherein the polymer is chosen from polyacrylates and alginates.

25. The composition as claimed in claim 24, wherein the polymer is a sodium polyacrylate or a sodium alginate.

26. The composition as claimed in claim 23, wherein the polymer is a polyacrylate having a molecular weight between 2000 and 50,000.

27. The composition as claimed in claim 23, wherein the polymer is a polyacrylate having a molecular weight between 3000 and 30,000.

28. The composition as claimed in claim 23, wherein the polymer is a polyacrylate having a molecular weight between 5000 and 20,000.

29. The composition as claimed in claim 23, wherein the polymer is in the solid phase.

30. The composition as claimed in claim 29, wherein the polymer represents from 1% to 5% by weight relative to the total weight of the solid phase.

31. The composition as claimed in claim 29, wherein the polymer represents from 2% to 4% by weight relative to the total weight of the solid phase.

32. The composition as claimed in claim 23, wherein the polymer is in the liquid phase.

33. The composition as claimed in claim 32, wherein the polymer represents from 0.2% to 10% by weight relative to the total volume of the liquid phase.

34. A method for preparing a cement starting from a composition as claimed in claim 5, comprising at least one step of mixing the solid phase with the liquid phase and in which the following reaction takes place:

$$6Ca_{(1-x)}Sr_xHPO_4 + y\, CaO \rightarrow Ca_{(10-6x)}Sr_{6x}(PO_4)_6(OH)_2 + (y-4)Ca(OH)_2.$$

35. A dental kit comprising a composition as claimed in claim 5 in the form of a liquid phase and a solid phase that are stored in separate compartments.

36. A method for filling a dental root canal comprising applying the composition as claimed in claim 5 to an open canal.

37. A method for capping pulp comprising applying the composition as claimed in claim 5 to a pulp thereby capping the pulp.

38. A method for repairing a perforation comprising applying the composition as claimed in claim 5 to a perforation.

39. A method for forming an apical plug comprising applying the composition as claimed in claim 5 to a perforation of a canal wall.

* * * * *